United States Patent [19]

Matsuno

[11] 3,957,895

[45] May 18, 1976

[54] METHOD FOR PRODUCING 5-ALKYLIDENENORBORNENE-2

[75] Inventor: Mitsuo Matsuno, Kawasaki, Japan

[73] Assignee: Nippon Oil Company Ltd., Tokyo, Japan

[22] Filed: Mar. 4, 1975

[21] Appl. No.: 555,089

[30] Foreign Application Priority Data

Mar. 5, 1974 Japan................................ 49-24793

[52] U.S. Cl. ......................................... 260/666 PY
[51] Int. Cl.² ........................................... C07C 5/24
[58] Field of Search ............................... 260/666 PY

[56] References Cited
UNITED STATES PATENTS 3,347,944  10/1967  Fritz et al. ..................... 260/666 PY Primary Examiner—Veronica O'Keefe
Attorney, Agent, or Firm—Wigman & Cohen

[57] ABSTRACT

A method for producing 5-alkylidenenorbornene-2 which is characterized in that 5-alkenylnorbornene-2 is isomerized in the presence of a compound catalyst prepared by the reaction between organic alkali metal compounds and water, and that the isomerization is carried out effectively and economically without using any expensive solvent.

6 Claims, No Drawings

METHOD FOR PRODUCING 5-ALKYLIDENENORBORNENE-2

BACKGROUND OF THE INVENTION

This invention relates to a method for producing 5-alkylidenenorbornene-2. More paticularly, the invention relates to a method for producing 5-alkylidenenorbornene-2 by isomerizing 5-alkenylnorbornene-2.

It is generally known that 5-alkylidenenorbornene-2 is used as the third component of the so-called EPDM rubber which is a copolymer of three materials, ethylene, propylene and nonconjugated diolefin. Further, it is also known that 5-alkylidenenorbornene-2 is produced by isomerization of 5-alkenylnorbornene-2. For the above isomerization, various kinds of methods have been proposed, for example, a method for isomerization using a catalyst of alkali metal-carrier type (U.S. Pat. No. 3,347,944); a method using a catalyst consisting of alkali metal strong base such as potassium hydroxide and an aprotic dipolar solvent such as dimethylsulfoxide (ibid.); a method using a catalyst of a mixture of a sodium-potassium alloy and hexamethylphosphortriamide (French Pat. No. 1,529,455); a method using a catalyst of a mixture of alkali metal amide such as sodium amide and a nitrogen-containing solvent such as ethylenediamine (French Pat. No. 1,534,366); and a method using an organic alkali metal catalyst (French Pat. No. 1,525,727) are known.

There are, however, several disadvantages in the above known methods that preparation of the catalyst is difficult, a large amount of catalyst is necessary as the catalytic activity is low, severe raction conditions such as a high reaction temperature are necessary, or a large quantity of expensive solvent which is difficult to separate from the product of 5-alkylidenenorbornene-2, must be used.

BRIEF SUMMARY OF THE INVENTION

In view of the above, the principal object of th present invention is to provide a novel and improved method for producing 5-alkylidenenorbornene-2 by isomerizing 5-alkenylnorbornene-2.

Another object of the present invention is to provide an improved method for producing 5-alkylidenenorbornene-2 using an effective and inexpensive catalyst.

Further object of the present invention is to provide an improved method for producing 5-alkylidenenorbornene-2 without the use of expensive solvents.

Pursuant to the above objects, the inventor of the present invention has carried out eager and extensive studies on the method for producing 5-alkylidenenorbornene-2 by isomerizing 5-alkenylnorbornene-2, as the result he has found out an inexpensive and very effective catalyst for such method. Thereby, the method of the present invention for economically producing 5-alkylidenenorbornene-2 has been accomplished.

That is, the method of the present invention for producing 5-alkylidenenorbornene-2 is characterized in that 5-alkenylnorbornene-2 is isomerized in the presence of a compound catalyst of organic alkali metal compounds and water.

DETAILED DESCRIPTION OF THE INVENTION

The above-mentioned 5-alkenylnorbornene-2 used for the method of the present invention is represented by the general formula:

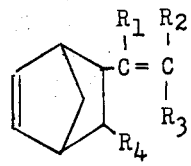

in which $R_1$, $R_2$, $R_3$ and $R_4$ are hydrogen or alkyl groups each having 1 to 6 carbon atoms such as methyl group, ethyl group, propyl group and the like. As the above compounds, there are, for example 5-vinylnorbornene-2, 5-isopropenylnorbornene-2, 5-butenylnorbornene-2, and 5-vinyl-6-methylnorbornene-2.

The organic alkali metal compounds used in the method of the present invention are represented by the general formula: R-M, where M is one member or a mixture of lithium, sodium and potassium, and R may be a radical usually having 1 to 20 carbon atoms selected from alkyl groups such as methyl, ethyl, propyl, butyl and pentyl groups; alkenyl groups such as allyl and methallyl groups; cycloalkyl groups such as cyclohexyl group; and aryl and aralkyl groups such as phenyl and benzyl groups. Further, the complexes of naphthalene, anthracene and other polycyclic aromatic compounds with lithium sodium and potassium can also be used as the organic alkali metal compounds. The above organic alkali metal compounds can be used solely or as a mixture of two or more.

The method for preparing the above-mentioned organic alkali metal compounds is not especially restricted, however, the reaction between hydrocarbon halides and alkali metals in hydrocarbon solvents, and the reaction between polycyclic aromatic compounds and alkali metals in polar solvents may be generally employed.

These organic alkali metal compounds can be prepared either separately from the isomerization or in the reaction mixture of the isomerization containing 5-alkenylnorbornene-2. Further, the existence of alkali metal salts such as LiCl, LiBr, NaCl, NaBr, KCl and KBr as the by-product of the organic alkali metal compounds and excess alkali metals such as lithium, sodium and potassium does not give any ill effect to the method of the present invention. In other words, the combination of the organic alkali metal compound and water is serviceable as an effective catalyst to the method of the present invention, and neither the combination of the alkali metal salt and water nor the combination of the alkali metal and water has any catalytic activity.

It is heretofore known that, in case water is added to organic alkali metal compounds, they are hydrolyzed to form alkali metal hydroxides, so that the deactivation of organic alkali metal compounds in several reactions is carried out by adding water to the reaction system.

While, the inventor has found the fact that, when a certain amount of water is added to the organic alkali metal compound, the catalystic activity of the compound for the isomerization is anything but lost, it is largely enhanced on the contrary. The method of the present invention is thus accomplished.

The water used for the activation of the organic alkali metal compounds may be pure water such as deionized water, city water, or sea water containing organic or inorganic compounds. The amount of water added to the organic alkali metal compound is 0.01 to 0.9 mole, preferably 0.1 to 0.8 mole to one mole of the organic alkali metal compound. In the preparation of the compound catalyst from the organic alkali metal compound and water, the organic alkali metal compound is sufficiently suspended or dissolved in a solvent by an appropriate means such as stirring, and water is then added so as to disperse well. Accordingly, when water is added, it may be previously dispersed or dissolved in a suitable solvent or it may be added as steam.

The solvents used for dispersing or dissolving the organic alkali metal compounds in the preparation of the compound catalyst may be those which do not deactivate the catalyst by reacting with the organic alkali metal compounds. As such solvents, for example, aliphatic hydrocarbons, aromatic hydrocarbons and 5-alkenylnorbornene-2 to be isomerized are preferable.

As the solvents for the dilution and addition of water, those which are miscible with water and neither decompose nor deactivate the organic alkali metal compounds can be used. For example, ethers having carbon atom number of from 2 to 20 such as diethyl ether, tetrahydrofuran, ethylene glycol dimethyl ether and tetrahydropyran; and tertiary amines having carbon atom number of from 3 to 20 such as triethylamine, N, N, N', N'-tetramethylethylenediamine, N,N'-dimethylpiperazine, triethylenediamine and N-methylmorphorine, are exemplified. Further, water can be used by dispersing in the solvents which do not dissolve water so much and are inactive to the organic alkali metal compounds. As such solvents, for example, there are aliphatic hydrocarbons and aromatic hydrocarbons.

Among those, however, tertiary amines are more preferable.

The reaction between the organic alkali metal compound and water is generally carried out at a temperature in the range of −40°C to 200°C, preferably from −20°C to 150°C. When the reaction temperature is too low, water is solidified to hinder the reaction and the reaction rate becomes very small, therefore, as a matter of fact, the preparation procedure of the catalyst can not be completed. On the contrary, when the temperature is too high, the organic alkali metal compound is decomposed and the pressure of the raction system is raised to excess, which is not desirable.

The quantity of the catalyst used for the isomerization of 5-alkenylnorbornene-2 in the method of the present invention is not especially restricted, however, it may be in the range of 0.1 millimole to 100 millimoles, preferably 0.5 millimole to 50 millimoles of the organic alkali metal compound to one mole of 5-alkenylnorbornene-2.

The isomerization of 5-alkenylnorbornene-2 using the catalyst of the present invention can be carried out without any solvent, however, the solvents which do not give any ill effect to the reaction such as aliphatic hydrocarbon or aromatic hydrocarbons can also be used.

The isomerization temperature of the method of the present invention using the compound catalyst is in the range of 0°C to 200°C, and preferably from 25°C to 150°C.

The reaction of the method of the present invention can be carried out under normal pressure or increased pressure through batch process, semi-batch process or continuous process. Further, in the method of the present invention, the un-reacted 5-alkenylnorbornene-2 is separated from 5-alkylidenenorbornene-2 by fractionation, and the former can be used again for the next isomerization.

In order that those skilled in the art may better understand the present invention and the manner in which it may be practiced, the following specific examples are given, which are intended as merely illusrative and in no way restrictive of the invention.

EXAMPLES 1 to 4 and COMPARATIVE EXAMPLE1

In the first place, 6 kg of 5-vinylnorbornene-2 was fed into a 10 liter stainless steel autoclave filled with nitrogen gas, and 200 g of sodium dispersion (sodium content: 35 g, dispersion medium: 5-ethylidenenorbornene-2) was added thereto. Then, 65 g of n-butyl chloride was added for 30 minutes while stirring well and carefully keeping the contents at a temperature lower than 20°C. Further, in each example 1 liter of thus prepared 5-vinylnorbornene-2 containing the dispersion of butylsodium was fed into a 2 liter stainless steel autoclave which had been well dried and displaced with nitrogen gas, and while stirring well and cooling below 20°C with ice water, a certain amount (indicated in Table 1) of deionized water was added and allowed to react for 30 minutes. This reaction mixture is then heated for 3 hours at 50°C, and a large quantity of water is added to deactivate the catalyst. The organic layer of each product was analyzed by gas chromatography, the results of which are shown in the following Table 1.

EXAMPLE 5 AND COMPARATIVE EXAMPLE 2

In these examples, 200 g of 5-vinylnorbornene-2 and 30 g of toluene dispersion containing 16 g of phenyl sodium were added to each 500 ml stainless steel autoclave, and 19 g of anhydrous N,N,N',N'-tetramethylethylenediamine was further added in Comparative Example 2, and 19 g of N,N,N',N'-tetramethylethylenediamine containing 1.4 g of water was added in Example 5, then the contents were allowed to react for 1 hour at 50°C. After the reaction, each catalyst was deactivated, and the organic layer was analyzed by gas chromatography. The results of the analysis are shown in the following Table 2.

EXAMPLE 6 AND COMPARATIVE EXAMPLE 3

In these examples, 120 g of 5-isopropenylnorbornene-2 and 40 ml of isooctane dispersion containing 2 g of phenyl sodium were fed into each 500 ml stainless steel autoclave. In Example 6, 10 ml of isooctane dispersion containing 0.18 g of water (isooctane dissolves only 0.0055% of water at 20°C) was further added to the above contents. The mixtures were immediately heated to 160°C and reacted for 3 hours. After the reaction, the autoclaves were cooled and the catalysts were deactivated. The products were then analyzed by gas chromatography, the results of which are shown in the following Table 3.

Table 1

| Example No. | Qt. of Deionized Water ml | H₂O/BuNa (Molar Ratio) | 5-Vinylnorbornene-2 (%) | 5-Ethylidenenorbornene-2 (%) | Others (%) |
|---|---|---|---|---|---|
| Example 1 | 0.18 | 0.1 | 78.1 | 21.9 | 0 |
| Example 2 | 0.45 | 0.25 | 45.3 | 54.7 | 0 |
| Example 3 | 0.90 | 0.50 | 37.8 | 62.2 | 0 |
| Example 4 | 1.35 | 0.75 | 13.5 | 86.5 | 0 |
| Comparative Example 1 | 0 | 0 | 86.2 | 13.8 | 0 |

Table 2

| Example No. | Tetramethylethylenediamine (g) | Water (g) | 5-Vinylnorbornene-2 (%) | 5-Ethylidenenorbornene-2 (%) | Others (%) |
|---|---|---|---|---|---|
| Example 5 | 19 | 1.4 | 48.6 | 51.4 | 0 |
| Comparative Example 2 | 19 | 0 | 69.3 | 30.6 | 0.1 |

Table 3

| Example No. | Qt. of Water (g) | H₂O/PhNa (Molar Ratio) | 5-Isopropenylnorbornene-2 (%) | 5-Isopropylidenenorbornene-2 (%) | Methyltetrahydroindene(*) (%) |
|---|---|---|---|---|---|
| Example 6 | 0.18 | 0.5 | 26.7 | 73.3 | Trace |
| Comparative Example 3 | 0 | 0 | 64.3 | 30.5 | 5.2 |

(*) 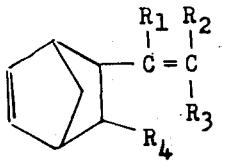

What is claimed is:

1. A method for producing 5-alkylidenenorbornene-2 comprising, isomerizing 5-alkenylnorbornene-2 using a compound catalyst obtained by the reaction between organic alkali metal compounds and water, the alkali metals of said organic alkali metal compounds being lithium, sodium and/or potassium and the quantity of water used is 0.01 to 0.9 mole to 1 mole of said organic alkali metal compound.

2. A method for producing 5-alkylidenenorbornene-2 as claimed in claim 1, in which said 5-alkenylnorbornene-2 is represented by the general formula:

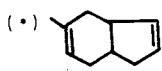

in which $R_1$, $R_2$, $R_3$ and $R_4$ are hydrogen or alkyl groups each having 1 to 6 carbon atoms.

3. A method for producing 5-alkylidenenorbornene-2 as claimed in claim 1, in which said 5-alkenylnorbornene-2 is at least a member selected from the group consisting of 5-vinylnorbornene-2, 5-isopropenylnorbornene-2, 5-butenylnorbornene-2 and 5-vinyl-6-methylnorbornene-2.

4. A method for producing 5-alkylidenenorbornene-2 as claimed in claim 1, in which said organic alkali metal compounds are represented by the general formula: R-M, where M is at least one member selected from the group consisting of lithium, sodium and potassium, and R is at least one member selected from the group consisting of alkyl groups, alkenyl groups, cycloalkyl groups, aryl groups and aralkyl groups having 1 to 20 carbon atoms.

5. A method for producing 5-alkylidenenorbornene-2 as claimed in claim 1, in which said isomerization is carried out in the presence of a member selected from ethers, tertiary amines, aliphatic hydrocarbons and aromatic hydrocarbons which is employed in the preparation of said compound catalyst.

6. A method for producing 5-alkylidenenorbornene-2 as claimed in claim 1, in which the quantity of water to said organic alkali metal compound to obtain said compound catalyst is, preferably 0.1 to 0.8 mole of water to 1 mole of said organic alkali metal compound.

* * * * *